US010321994B2

(12) United States Patent
Erzberger et al.

(10) Patent No.: US 10,321,994 B2
(45) Date of Patent: Jun. 18, 2019

(54) HEART VALVE WITH STENT HAVING VARYING CELL DENSITIES

(71) Applicant: St. Jude Medical, Cardiology Division, Inc., St. Paul, MN (US)

(72) Inventors: Gary Erzberger, Plymouth, MN (US); Yousef F. Alkhatib, Edina, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 9 days.

(21) Appl. No.: 15/591,304

(22) Filed: May 10, 2017

(65) Prior Publication Data

US 2017/0325944 A1 Nov. 16, 2017

Related U.S. Application Data

(60) Provisional application No. 62/336,272, filed on May 13, 2016.

(51) Int. Cl.
*A61F 2/24* (2006.01)

(52) U.S. Cl.
CPC ...... *A61F 2/2418* (2013.01); *A61F 2230/008* (2013.01); *A61F 2230/0054* (2013.01);
(Continued)

(58) Field of Classification Search
CPC .. A61F 2/2418; A61F 2/07; A61F 2/89; A61F 2/848; A61F 2230/0054;
(Continued)

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| CN | 101961273 B | 11/2012 |
| DE | 19857887 B4 | 5/2005 |

(Continued)

OTHER PUBLICATIONS

International Search Report for Application No. PCT/US2017/031853, dated Aug. 3, 2017.

(Continued)

*Primary Examiner* — Christopher D. Prone
*Assistant Examiner* — Tiffany P Shipmon
(74) *Attorney, Agent, or Firm* — Lerner, David, Littenberg, Krumholz & Mentlik, LLP

(57) ABSTRACT

A prosthetic heart valve for replacing a native valve includes a collapsible and expandable stent extending between a proximal end and a distal end, the stent including an annulus section adjacent the proximal end and an aortic section adjacent the distal end. The annulus section has cells arranged in at least one annulus row, each annulus row having a same first number of cells, the first number defining a first cell density. The aortic section has cells arranged in at least one aortic row, each aortic row having a same second number of cells, the second number defining a second cell density, the first cell density and the second cell density being different. A valve assembly is disposed within the stent.

15 Claims, 8 Drawing Sheets

(52) U.S. Cl.
CPC ............... *A61F 2250/0015* (2013.01); *A61F 2250/0036* (2013.01)

(58) Field of Classification Search
CPC ...... A61F 2250/0015; A61F 2220/0016; A61F 2002/075
USPC ...................................................... 623/1.14
See application file for complete search history.

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| 8,840,663 B2 | 9/2014 | Salahieh et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0210304 A1 | 10/2004 | Seguin et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0112309 A1 | 4/2009 | Jaramillo et al. |
| 2009/0138079 A1 | 5/2009 | Tuval et al. |
| 2009/0287299 A1* | 11/2009 | Tabor ............... A61F 2/013 623/1.26 |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |

(56) References Cited

U.S. PATENT DOCUMENTS

| | | |
|---|---|---|
| 2010/0298931 A1 | 11/2010 | Quadri et al. |
| 2011/0029072 A1 | 2/2011 | Gabbay |
| 2011/0238168 A1* | 9/2011 | Pellegrini ............. A61F 2/2412 623/2.17 |
| 2011/0264196 A1* | 10/2011 | Savage ................ A61F 2/2418 623/1.26 |
| 2012/0303116 A1 | 11/2012 | Gorman, III et al. |
| 2015/0209140 A1* | 7/2015 | Bell ..................... A61F 2/2418 623/2.18 |
| 2015/0272737 A1 | 10/2015 | Dale et al. |

FOREIGN PATENT DOCUMENTS

| | | |
|---|---|---|
| DE | 10121210 B4 | 11/2005 |
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1926455 A2 | 6/2008 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 2001028459 A1 | 4/2001 |
| WO | 2001049213 A2 | 7/2001 |
| WO | 0154625 A1 | 8/2001 |
| WO | 2001056500 A2 | 8/2001 |
| WO | 200176510 A2 | 10/2001 |
| WO | 0236048 A1 | 5/2002 |
| WO | 0247575 A2 | 6/2002 |
| WO | 2002067782 A2 | 9/2002 |
| WO | 2003047468 A1 | 6/2003 |
| WO | 2005070343 A1 | 8/2005 |
| WO | 06073626 A2 | 7/2006 |
| WO | 2007071436 A2 | 6/2007 |
| WO | 08070797 A2 | 6/2008 |
| WO | 2009094188 A2 | 7/2009 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2015179468 A1 | 11/2015 |

OTHER PUBLICATIONS

Andersen, H. R., et al., "Transluminal implantation of artificial heart valves", European Heart Journal, (1992), vol. 13, Issue 5, 704-708.
Andersen, Henning Rud, "Transluminal Catheter Implanted Prosthetic Heart Valves", International Journal of Angiology 7:102-106, 1998.
Braido et al., U.S. Appl. No. 29/375,243, filed Sep. 20, 2010, titled "Surgical Stent Assembly".
Braido, U.S. Appl. No. 29/375,260, filed Sep. 20, 2010, titled "Forked Ends".
Christoph H. Huber, et al., "Direct-Access Valve Replacement", Journal of the American College of Cardiology, vol. 16, No. 2, (Jul. 19, 2005).
Dewey et al., "Transapical aortic valve implantation: an animal feasibility study"; The annals of thoracic surgery 2006; 82: 110-6 (Feb. 13, 2006).
John G. Webb et al., "Percutaneous Aortic Valve Implantation Retrograde From the Femoral Artery", Circulation, 2006; 113:842-850 (Feb. 6, 2006).
Knudsen, LL. et al., "Catheter-implanted prosthetic heart valves", The International Journal of Artificial Organs, vol. 16, No. 5, 1993, pp. 253-262.
M. J. Mack, "Minimally invasive cardiac surgery", Surgical Endoscopy, 2006, 20:S488-S492, DOI: 10.1007/s00464-006-0110-8 (presented Apr. 24, 2006).
Moazami, Nader, et al., "Transluminal Aortic Valve Placement", ASAIO Journal, (1996); 42:M381-M385.
Quaden, Rene et al., "Percutaneous aortic valve replacement: resection before implantation", 836-840, European J. of Cardio-thoracic Surgery, 27 (2005).
Ruiz, Carlos, "Overview of PRE-CE Mark Transcatheter Aortic Valve Technologies", Euro PCR, dated May 25, 2010.
Samuel V. Lichtenstein et al., "Transapical Transcatheter Aortic Valve Implantation in Humans", Circulation. 2006; 114: 591-596 (Jul. 31, 2006).
Samuel V. Lichtenstein, "Closed heart surgery: Back to the future", The Journal of Thoracic and Cardiovascular Surgery, 2006, vol. 131, No. 5, pp. 941-943.
Textbook "Transcatheter Valve Repair", 2006, pp. 165-186.
Walther et al., "Transapical approach for sutureless stent-fixed aortic valve implantation: experimental results", European Journal of Cardio-thoracic Surgery 29 (2006) 703-708 (Jan. 30, 2006).
Zegdi, Rachid, MD, PhD et al., "Is It Reasonable to Treat All Calcified Stenotic Aortic Valves With a Valved Stent?", 579-584, J. of the American College of Cardiology, vol. 51, No. 5, Feb. 5, 2008.

* cited by examiner

US 10,321,994 B2

HEART VALVE WITH STENT HAVING VARYING CELL DENSITIES

CROSS-REFERENCE TO RELATED APPLICATIONS

The present application claims the benefit of the filing date of U.S. Provisional Patent Application No. 62/336,272 filed May 13, 2016, the disclosure of which is hereby incorporated herein by reference.

BACKGROUND OF THE INVENTION

The present disclosure relates in general to heart valve replacement and, in particular, to collapsible prosthetic heart valves. More particularly, the present disclosure relates to stents for heart valves having variable cell density and to methods for creating same.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

SUMMARY OF THE INVENTION

In some embodiments, a prosthetic heart valve for replacing a native valve includes a collapsible and expandable stent extending between a proximal end and a distal end, the stent including an annulus section adjacent the proximal end, the annulus section having cells arranged in at least one annulus row, each said annulus row having a same first number of cells, the first number defining a first cell density, and an aortic section adjacent the distal end, the aortic section having cells arranged in at least one aortic row, each said aortic row having a same second number of cells, the second number defining a second cell density, the first cell density and the second cell density being different, and a valve assembly disposed within the stent.

In some embodiments, a collapsible and expandable stent for a prosthetic heart valve, the stent having a proximal end and a distal end includes an annulus section adjacent the proximal end, and the annulus section having cells arranged in at least one annulus row, each said annulus row having a same first number of cells, the first number defining a first cell density, and an aortic section adjacent the distal end, the aortic section having cells arranged in at least one aortic row, each said aortic row having a same second number of cells, the second number defining a second cell density, the first cell density and the second cell density being different.

BRIEF DESCRIPTION OF THE DRAWINGS

Various embodiments in accordance with the present disclosure will now be described with reference to the appended drawings. It is to be appreciated that these drawings depict only some embodiments and are therefore not to be considered limiting of its scope.

DETAILED DESCRIPTION

Inaccurate deployment and anchoring of a prosthetic heart valve in a patient may result in the leakage of blood between the implanted heart valve and the native valve annulus, commonly referred to as paravalvular leakage (also known as "perivalvular leakage"). In aortic valves, this leakage enables blood to flow from the aorta back into the left ventricle, reducing cardiac efficiency and putting a greater strain on the heart muscle. Additionally, calcification of the aortic valve and/or anatomical variations from one patient to another may affect the performance of the prosthetic valve and the interaction between the implanted valve and the calcified tissue is believed to be relevant to leakage, as will be outlined below. There is a need for further improvements to the devices, systems, and methods for positioning and sealing collapsible prosthetic heart valves during implantation in a patient. Specifically, there is a need for further improvements to the devices, systems, and methods for accurately implanting a prosthetic heart valve. Among other advantages, the present disclosure may address one or more of these needs.

As used herein, the terms "proximal" and "distal," when used in connection with a prosthetic heart valve, refer to the inflow and outflow ends, respectively, of the heart valve corresponding to natural circulation of blood through a healthy heart.

Figure 1:
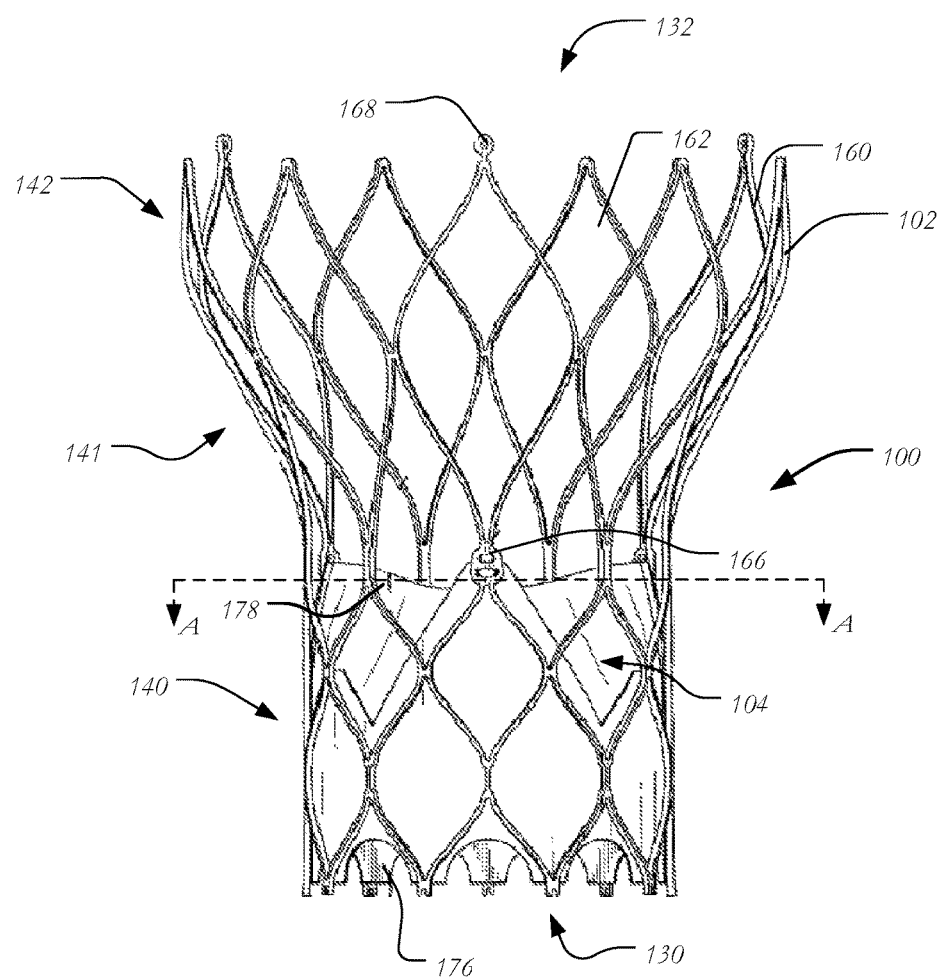
FIG. 1 is a side elevational view of a conventional prosthetic heart valve.

The stent of the present disclosure may be used in connection with prosthetic heart valves. FIG. 1 shows one such stent-supported prosthetic heart valve 100 including an expandable stent 102 and a valve assembly 104 as is known in the art. Prosthetic heart valve 100 is designed to replace a native tricuspid valve of a patient, such as a native aortic valve. It should be noted that while the embodiments discussed herein relate predominantly to prosthetic aortic valves having a stent with a shape as illustrated in FIG. 1, the general principles disclosed may be equally applied to a bicuspid valve, such as the mitral valve, and the stent could have different shapes, such as a flared or conical annulus section, a less-bulbous aortic section, and the like, and a differently shaped transition section.

Stent 102 may be formed from biocompatible materials that are capable of self-expansion, such as, for example, shape memory alloys, such as the nickel-titanium alloy known as "Nitinol" or other suitable metals or polymers. Stent 102 extends from proximal or annulus end 130 to distal or aortic end 132, and includes annulus section 140 adjacent proximal end 130, transition section 141 and aortic section 142 adjacent distal end 132. Annulus section 140 may have a relatively small cross-section in the expanded configuration, while aortic section 142 may have a relatively large cross-section in the expanded configuration. Preferably, annulus section 140 is in the form of a cylinder having a substantially constant diameter along its length. Transition section 141 may taper outwardly from annulus section 140 to aortic section 142. Each of the sections of stent 102 includes a plurality of struts 160 forming diamond-shaped cells 162 connected to one another in one or more annular rows around the stent. For example, as shown in FIG. 1, annulus section 140 may have two annular rows of complete cells 162 and aortic section 142 and transition section 141 may each have one or more annular rows of partial cells 162. Cells 162 in aortic section 142 may be larger than cells 162 in annulus section 140. The larger cells in aortic section 142 better enable prosthetic valve 100 to be positioned in the native valve annulus without the stent structure interfering with blood flow to the coronary arteries.

Stent 102 may include one or more retaining elements 168 at distal end 132 thereof, retaining elements 168 being sized and shaped to cooperate with female retaining structures (not shown) provided on a deployment device. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Prosthetic heart valve 100 includes valve assembly 104 preferably secured to stent 102 in annulus section 140. Valve assembly 104 includes cuff 176 and a plurality of leaflets 178 which collectively function as a one-way valve by coapting with one another. As a prosthetic aortic valve, valve 100 has three leaflets 178. However, it will be appreciated that other prosthetic heart valves with which the stent of the present disclosure may be used may have a greater or lesser number of leaflets.

Although cuff 176 is shown in FIG. 1 as being disposed on the luminal or inner surface of annulus section 140, it is contemplated that, with the stent configurations disclosed herein, the cuff may be disposed on the abluminal or outer surface of the annulus section or may cover all or part of either or both of the luminal and abluminal surfaces. Cuff may also have a loose fit and incorporate longitudinal and/or circumferential pleats, folds or other elements to aid in paravalvular leakage. Both cuff 176 and leaflets 178 may be wholly or partly formed of any suitable biological material or polymer such as, for example, polyethylene terephthalate (PET), ultra-high-molecular-weight polyethylene (UHMWPE), or polytetrafluoroethylene (PTFE).

Leaflets 178 may be attached along their lower belly portions to cells 162 of stent 102, with the commissure between adjacent leaflets 178 attached to commissure features 166. As can be seen in FIG. 1, each commissure feature 166 may lie at the intersection of four cells 162, two of the cells being adjacent one another in the same annular row, and the other two cells being in different annular rows and lying in end-to-end relationship. In other stent configurations, however, this need not be the case, and the commissure feature need not lie at the intersection of four cells. Preferably, commissure features 166 are positioned entirely within annulus section 140 or at the juncture of annulus section 140 and transition section 141. Commissure features 166 may include one or more eyelets which facilitate the suturing of the leaflet commissure to stent 102 and can be of any geometric shape that is driven by the number and orientation of holes needed for suturing.

Prosthetic heart valve 100 may be used to replace a native aortic valve, another transcatheter valve, a surgical heart valve or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed configuration. The delivery device may be introduced into a patient using a transfemoral, transaortic, transsubclavian, transapical, transseptal or any other percutaneous approach. Once the delivery device has reached the target site, the user may deploy prosthetic heart valve 100. Upon deployment, prosthetic heart valve 100 expands so that annulus section 140 is in secure engagement within the native aortic annulus and native calcified leaflets. When prosthetic heart valve 100 is properly positioned inside the patient's aortic annulus, it works as a one-way valve, allowing blood to flow from the left ventricle of the heart to the aorta, and preventing blood from flowing in the opposite direction into the ventricle.

Figure 2:
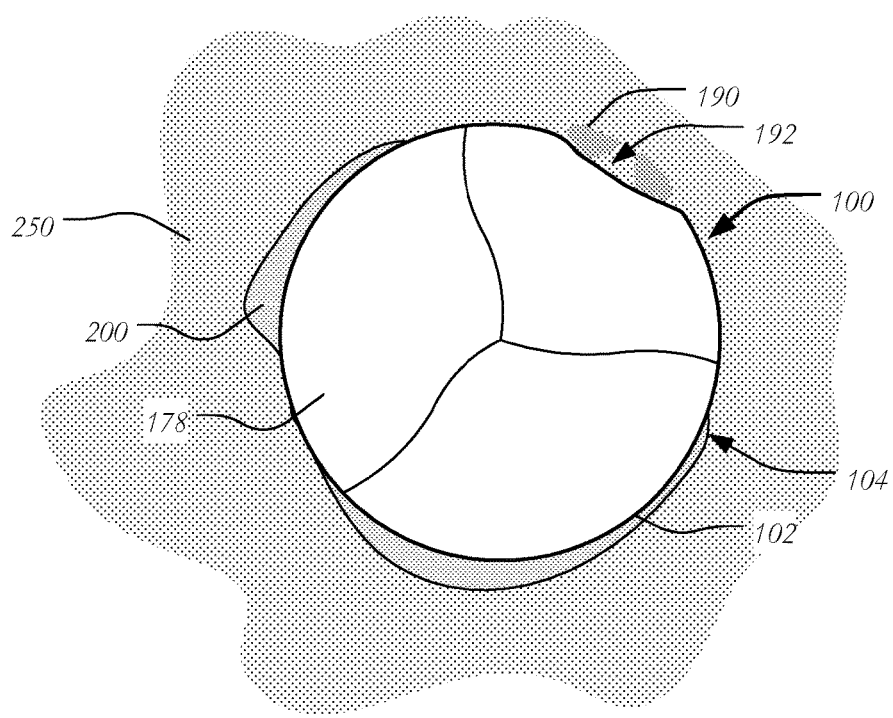
FIG. 2 is a highly schematic cross-sectional view taken along line A-A of FIG. 1 and showing the prosthetic heart valve disposed within a native valve annulus.

FIG. 2 is a highly schematic cross-sectional illustration of prosthetic heart valve 100 disposed within native valve annulus 250. As seen in the figure, valve assembly 104 has a substantially circular cross-section which is disposed within the non-circular native valve annulus 250. It will be understood that while prosthetic heart valve 100 is shown with a circular cross-section for the sake of clarity, certain portions will deflect to accommodate the geometry in the anatomy. Alternatively, heart valve 100 may have an elliptical or D-shaped cross-section for use in mitral, tricuspid, or diseased bicuspid valve applications. At certain locations around the perimeter of heart valve 100, gaps 200 form between heart valve 100 and native valve annulus 250. Blood flowing through these gaps and past valve assembly 104 of prosthetic heart valve 100 can cause regurgitation and other inefficiencies which reduce cardiac performance. Such improper fitment may be due to suboptimal native valve annulus geometry due, for example, to calcification of native valve annulus 250 or to irregularities in unresected native leaflets.

Additionally, in this illustration, two calcium nodules 190 are disposed near the circumference of the heart valve, the calcium nodules limiting the proper expansion of heart valve 100. As previously discussed, stent 102 is typically crimped during delivery and allowed to expand within the native vale annulus. This expansion of the stent 102 includes an expansion of each individual cell 162. In some cases, calcium nodules prevent the expansion of one or more of the cells 162 of the stent resulting in a warped or under-expanded region 192 of stent 102. This non-circular or unintended configuration may, in turn, affect the functioning of valve assembly 104, which is disposed within stent 102.

It has been learned that the presence of calcium nodules affects the ability of stent 102 to properly expand. Additionally, it has been learned that the density of cells—that is, the number of cells per row of cells formed by stent 102—will also affect the expansion of the stent. A greater cell density may result in a stent that expands with greater radial force and that is more rigid once expanded, reducing the risk of under-expansion of the stent. Additionally, if one or more calcium nodules prevent the full expansion of one of the cells of the stent, a greater cell density in a row will reduce the effects of the under-expanded cell on the overall geometry of the stent and the valve assembly disposed therein. Thus, it has been discovered that, in general, a higher cell density is better in dealing with the effects of under-expansion of cells due to calcium nodules.

On the other hand, it has also been discovered that an increased number of cells or struts may lead to other forms of leakage due to microchannels formed between the rigid struts and the native valve annulus, for example, the calcium nodules present on the native leaflets and/or annulus. A high cell density also may reduce blood flow to the coronary arteries or other blood flow, or the accessibility of guidewires and other devices.

Prior art stent configurations do not recognize this problem. For example, some transcatheter prosthetic heart valves have balloon-expandable stents and are forcibly expanded within the native valve annulus. While such a technique may address underexpansion, by way of remodeling the patient annulus, it involves a slightly more complicated procedure and requires the use of a balloon that is correctly positioned to expand the prosthetic heart valve instead of the self-expanding prosthetic heart valves described herein. This could also increase the risk of annulus rupture if all patient anatomical factors are not carefully considered. Alternatively, some self-expanding stent designs simply have an increased number of cells to increase stent rigidity, but show no recognition of the problems associated with microchanneling and a reduction in sealing performance along with the coronary access challenges.

Figure 3A:
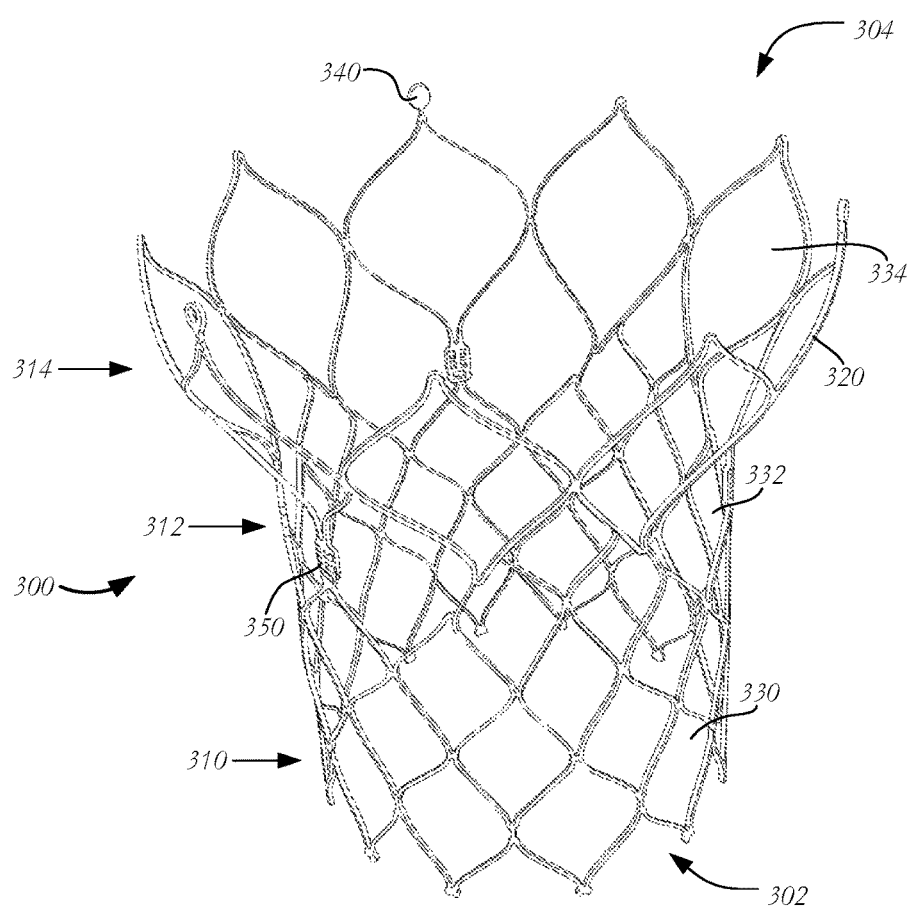
FIG. 3A is a perspective view of one example of a stent for a prosthetic heart valve having a varying cell density.

FIG. 3A shows one example of a self-expanding stent 300 to address this problem. Stent 300 may be formed from biocompatible materials that are capable of self-expansion, such as, for example, shape memory alloys, such as the Nitinol or other suitable metals or polymers. Stent 300 extends from proximal or annulus end 302 to distal or aortic end 304, and includes annulus section 310 adjacent proximal end 302, transition section 312 and aortic section 314 adjacent distal end 304. Annulus section 310 may have a relatively small cross-section in the expanded configuration, while aortic section 314 may have a relatively large cross-section in the expanded configuration. Preferably, annulus section 310 is in the form of a cylinder having a substantially constant diameter along its length but can utilize other shapes and configurations. Transition section 312 may taper outwardly from annulus section 310 to aortic section 314. Each of the sections of stent 300 includes a plurality of struts 320 forming cells 330,332,334 connected to one another in one or more annular rows around the stent. For example, as shown in FIG. 3A, annulus section 310 may have three annular rows of complete first cells 330 and aortic section 314 and transition section 312 may each have one or more annular rows of second and third full cells 332,334 or partial cells. Third cells 334 in aortic section 314 may be larger than first cells 330 in annulus section 310. The larger third cells 334 in aortic section 314 better enable stent 300 to be positioned in the native valve annulus without the stent structure interfering with blood flow to the coronary arteries.

Stent 300 may include one or more retaining elements 340 at distal end 304 thereof, retaining elements 340 being sized and shaped to cooperate with female retaining structures (not shown) provided on a deployment device. The engagement of retaining elements 340 with the female retaining structures on the deployment device helps maintain stent 300 in assembled relationship with the deployment device, minimizes longitudinal movement of the stent relative to the deployment device during unsheathing or resheathing procedures, and helps prevent rotation of the stent relative to the deployment device as the deployment device is advanced to the target location and the heart valve deployed. A number of commissure features 350 are also provided for attaching a valve assembly to the stent as described above.

Figure 3B:
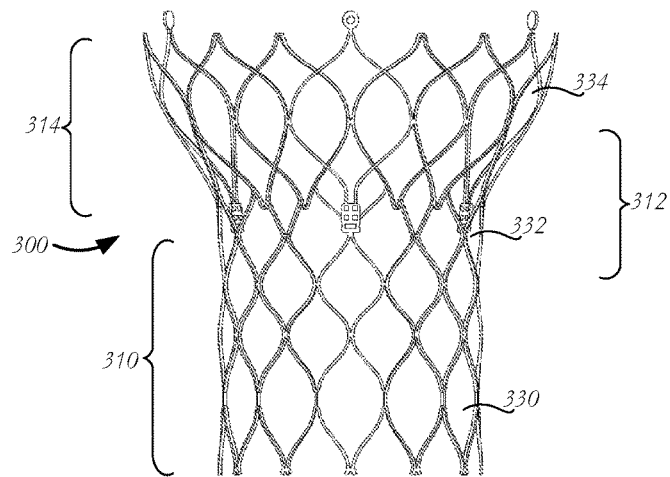
FIGS. 3B-G are front, back, left, right, bottom and top views of the stent of FIG. 3A.
Figure 3C:
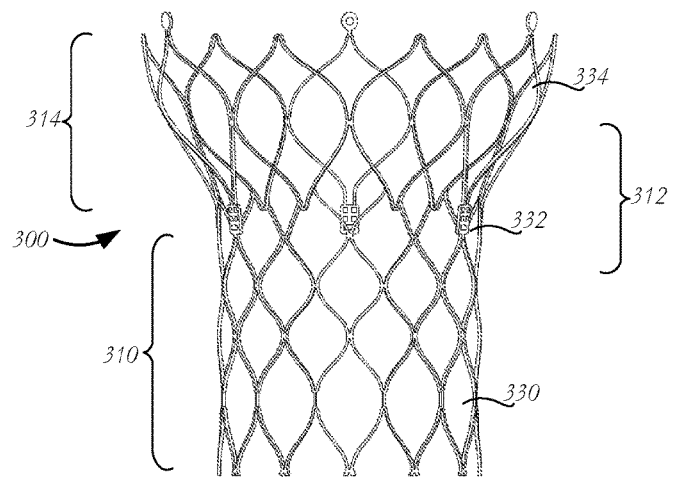

As best seen in the front and back views of FIGS. 3B-C, each row of cells in annulus section 310 has a greater number of smaller first cells 330 than the number of larger third cells 334 in each row of cells in aortic section 314. In other words, the cell density of rows comprising first cells 330, referred to herein as the first cell density, is greater than the cell density of rows comprising third cells 334, referred to herein as the second cell density. In the example shown, the first cell density is equal to twelve cells per row and the second cell density is equal to nine cells per row. The relatively higher first cell density provides a greater radial force and reduces the effect of an underexpanded cell on the performance of a valve, while the relatively lower second cell density minimizes interference with blood flow, such as coronary access flow, and provides better access by guidewires or other tools during or after an implantation procedure. Transition section 312 including second cells 332 may be disposed in several rows having one or more cell densities that are different from the first cell density and the second cell density.

Figure 3D:
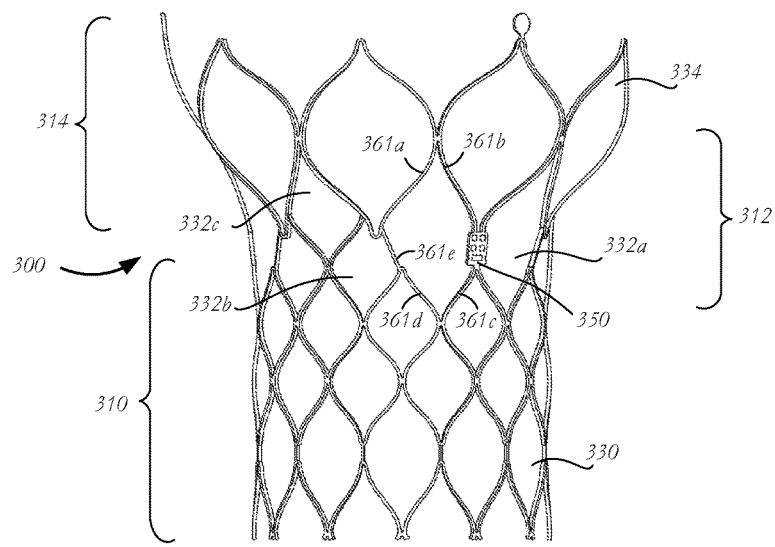
Figure 3E:
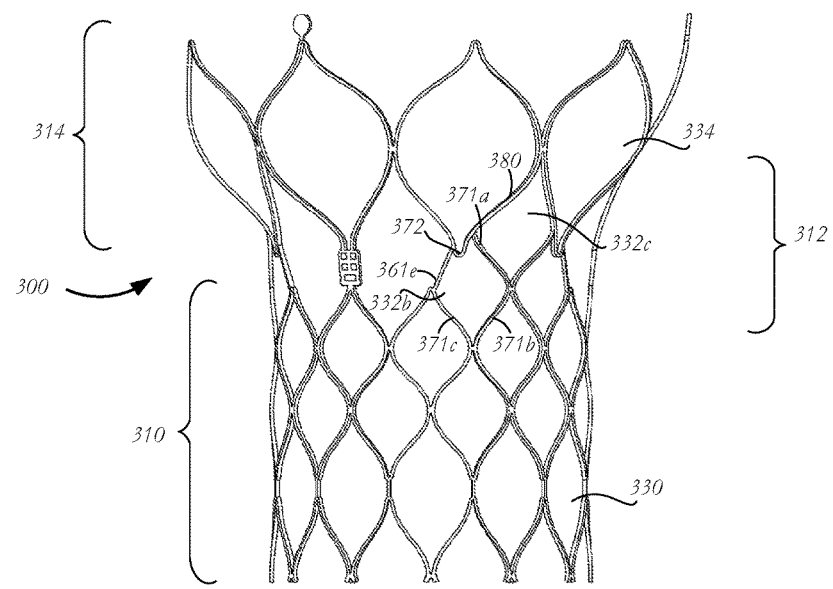
Figure 3F:
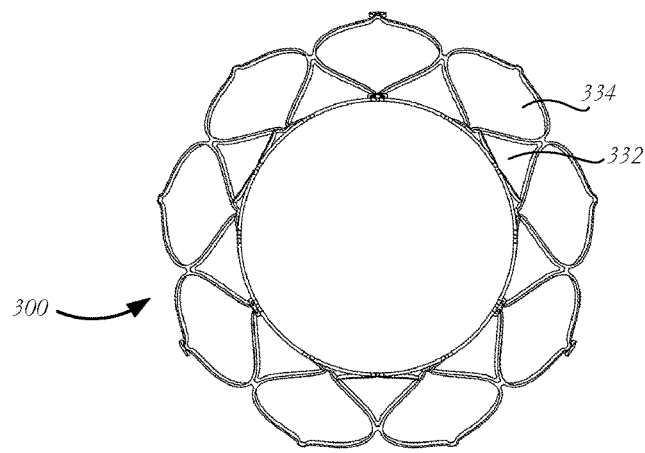
Figure 3G:
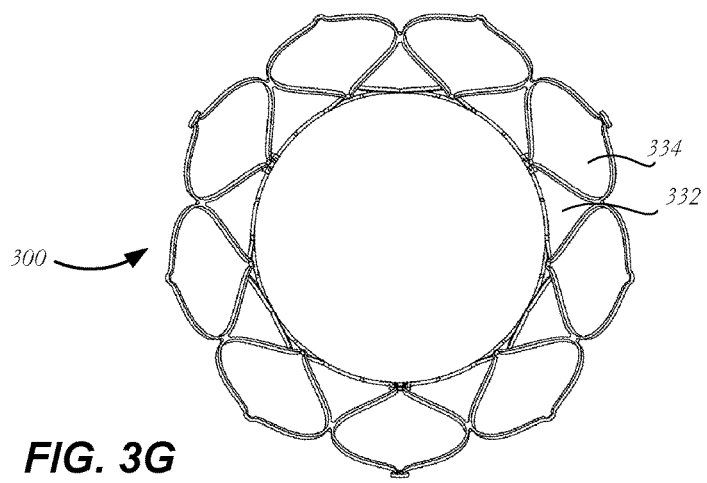

While first cells 330 and third cells 334 may be generally diamond-shaped cells, second cells 332a,332b,332c of transition section 312 may have other shapes as best seen in the side views of FIGS. 3D-E. Relatively large oversized second cells 332a are disposed on each side of commissure features 350 so that between each pair of commissure features 350 are two oversized second cells 332a. Each oversized second cell 332a has an asymmetric shape formed by five struts 361a-e and commissure feature 350. Struts 361a,361b may be shared struts that also form part of third cells 334 in aortic section 314. Likewise, struts 361c,361d may be shared struts that also form part of first cells 330 in annulus section 310. Finally, strut 361e may be a shared strut with an adjacent second cell 332b, strut 361e being different from the remaining struts by connecting to struts 361a and 361d at positions spaced from their respective ends. In other words, while most of the struts of stent 300 connect to one another at the apices of other cells, strut 361e of the transition section does not, as it compensates for the asymmetry of the cell as well as the presence of commissure feature 350 on the opposite side. It will be understood that this asymmetry is only one possible configuration, and that other configurations not having this asymmetry are possible and that all or some of the struts may be connected to apices.

Turning to FIG. 3E, between each two oversized second cells 332a are two lower second cells 332b and one symmetric upper second cell 332c. Lower second cells 332b also have an asymmetric shape defined by four struts that are shared with other cells as well as a protuberance of a third cell 334. Specifically, strut 371a is shared with a neighboring upper second cell 332c, struts 371b,371c are shared with first cells 330 in annulus section 310, and strut 361e is shared with oversized second cell 332a as previously discussed. A curved protuberance 372 of a third cell 334 in aortic section 314 also forms a portion of lower cell 332b. As for symmetric upper second cell 332c, it is generally diamond shaped and defined by four struts, two struts 380 that are shared with neighboring third cells 334 in aortic section 314 and two struts 371a, each of which is shared with one of the two lower asymmetric second cells 332b.

The foregoing arrangement of cells provides a stent 300 having an annulus section with twelve cells in each row; a transition section 312 having one row with six full cells and six substantially half cells and another row with three full cells and six substantially half cells; and an aortic section 314 with nine full cells. This arrangement of cells provides a transition of the cell density from twelve in the annulus section 310 to nine in the aortic section 314.

Optionally, struts 371a forming the lower V-shape of symmetric upper second cell 332c may have a thickness that is less than the thickness of all the other struts of stent 300. This reduced thickness of struts 371a may allow for even collapsing and expanding of the stent despite the asymmetry of some of the cells and the odd number of cells in certain sections of the stent.

Figure 4A:
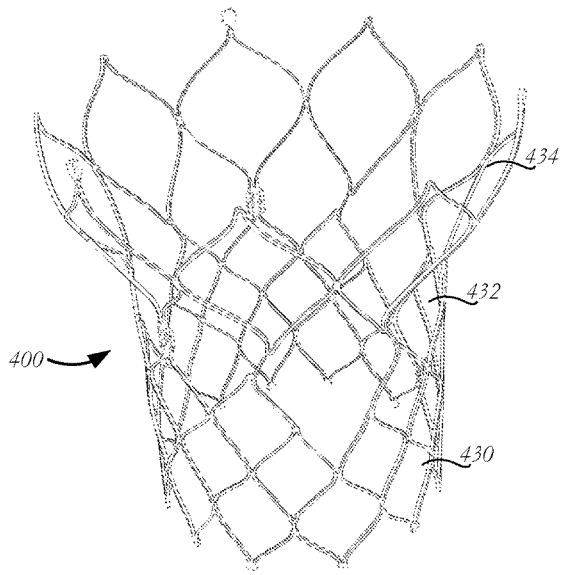
FIGS. 4A-B are perspective and front views of another example of a stent for a prosthetic heart valve having a varying cell density.
Figure 4B:
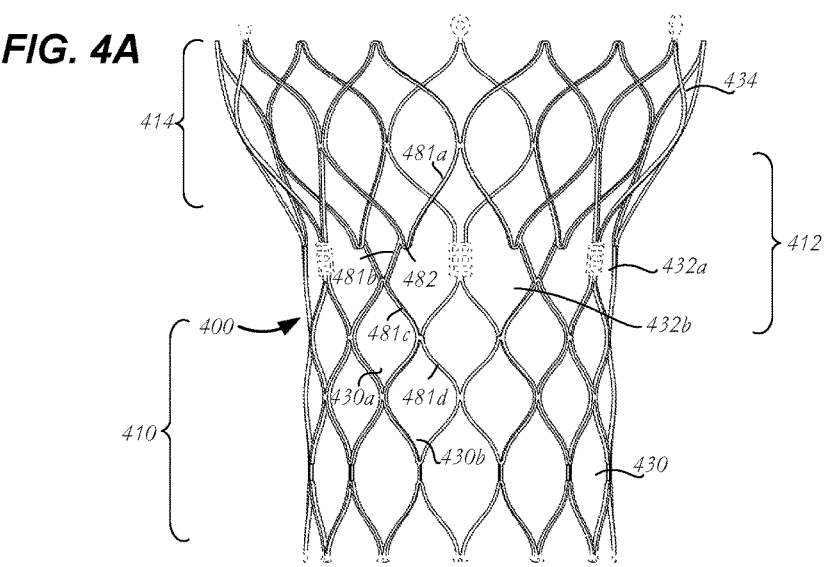

Variations in the stent configuration are possible while maintaining the overall relationship of cell densities in the annulus and aortic sections. For example, FIGS. 4A-B illustrate one variant of the stent in which the transition section has been modified. Elements similar to those of FIGS. 3A-G are shown as having like numbers preceded by a "4". In this variant, stent 400 is similar to stent 300 in every way except for transition section 412, which includes two oversized asymmetric second cells 432a that are similar to oversized second cells 332a, and enlarged generally diamond-shaped cells 432b, defined by struts 481a-d and protuberance 482 (there are two of each strut and each protruberance in each cell as cells 432b are symmetrical). Specifically, each half of enlarged cell 432b includes strut 481a that is shared with a neighboring third cell 434 in aortic section 414, strut 481b that is shared with an adjacent oversized asymmetric second cell 432a, strut 481c that is shared with one of first cells 430a in annulus section 410, and strut 481d that is shared with another first cell 430b in annulus section 410, struts 481c and 481d being substantially aligned with one another linearly. Protuberance 482 of a third cell 434 also forms part of enlarged cell 432b. Although enlarged cell 432b is described as being a part of transition section 412, as shown in FIGS. 4A-B, it may be considered to be part of annulus section 410 as well.

The foregoing arrangement of cells provides a stent 400 having an annulus section 410 with two rows of cells each having twelve cells, and a third row of cells having nine full cells and three partial cells; a transition section 412 having six full cells and three partial cells; and an aortic section 414 having nine full cells. This arrangement of cells provides a transition of cell density from a cell density of twelve in the annulus section 410 to a cell density of nine in the aortic section 414 that is different from the transition provided by stent 300.

Figure 5A:
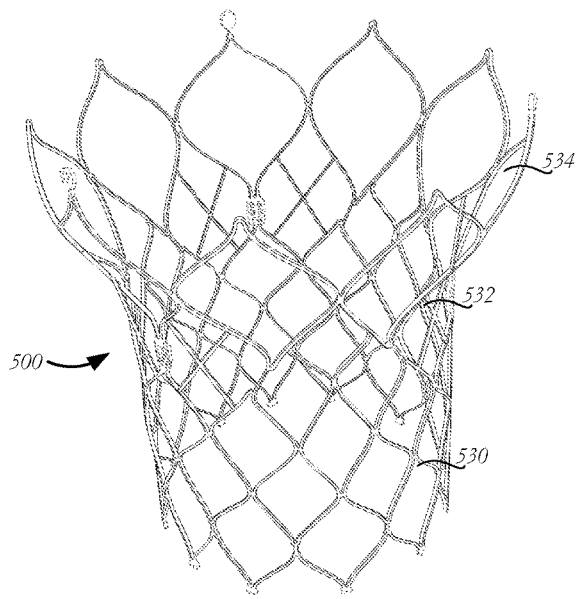
FIGS. 5A-B are perspective and front views of yet another example of a stent for a prosthetic heart valve having a varying cell density.
Figure 5B:
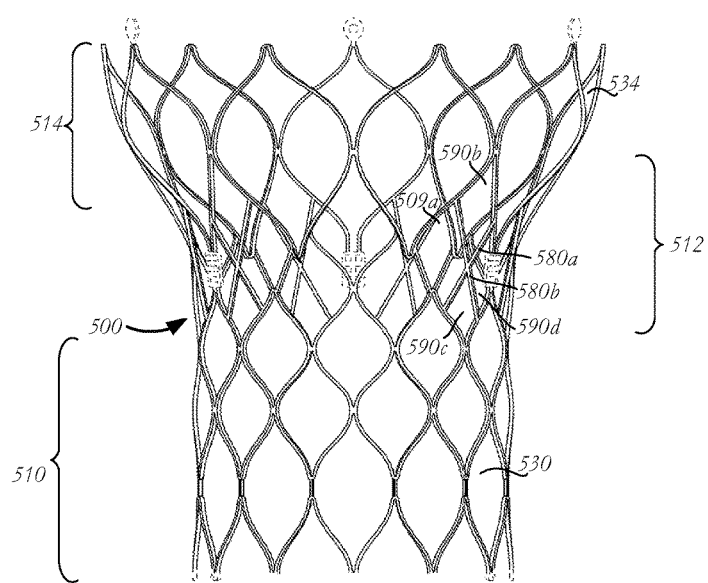

Another variant is shown in FIGS. 5A-B. In this variant, stent 500 is similar to stent 300 in every way except for transition section 512, and specifically the splitting of oversized second cells 332a into four cells as shown. Specifically, two additional struts 580a,580b generally form an X-shape, splitting the area previously occupied by oversized second cells 332a in the embodiment of FIGS. 3A-G into four cells 590a-d.

The arrangement of cells described above provides a stent 500 having an annular section 510 with three rows of cells each having twelve cells; a transition section 512 having a row of cells having twelve cells, a second row of cells having twelve full cells and three partial cells, and a third row of cells having six full cells and three partial cells; and an aortic section 514 having nine full cells. This arrangement of cells provides a transition of cell density from a cell density of twelve in the annular section 510 to a cell density of nine in the aortic section 514 that is different from the transition provided by both stents 300 and 400.

Thus, the transition section may be modified in a number of ways to bridge between the annulus sections 310,410,510 and the aortic sections 314,414,514, which have different cell densities, retaining the benefits of a larger density near the annulus section and the relatively smaller density near the aortic section.

While the devices disclosed herein have been described for use in connection with heart valve stents having a particular shape, the stent could have different shapes, such as a flared or conical annulus section, a less-bulbous aortic section, and the like, as well as a differently shaped transition section. Additionally, though the stents have been described in connection with expandable transcatheter aortic valve replacement, they may also be used in connection with other expandable cardiac valves, as well as with other devices in which it is desirable to create a seal between the periphery of the device and the adjacent body tissue, while at the same time not interfering with other body structures.

Moreover, although the disclosures herein have been described with reference to particular embodiments, it is to be understood that these embodiments are merely illustrative of the principles and applications of the present disclosure. For example, each of annulus section, transition section and aortic section may include any number of rows of cells as desired. Additionally, a stent may be formed that transitions from a low cell density to a high cell density and then back to a low cell density, or vice versa. Thus, multiple transition sections may be added to transition between two, three, four, five, six, seven or even eight cell densities, some or all of the cell densities being different than others. For example, a stent may have rows of nine cells adjacent the proximal end, then transition to rows of twelve cells, and then back to rows of nine cells at the distal end. Another stent may transition from rows of twelve cells to rows of nine cells and back to rows of twelve cells. Additionally, a stent may be formed that has a different cell density for each row of cells, or section of cells.

It is therefore to be understood that numerous modifications may be made to the illustrative embodiments and that other arrangements may be devised without departing from the spirit and scope of the present claims. For example, a prosthetic heart valve for replacing a native valve may include a stent including an annulus section adjacent the proximal end, the annulus section having cells arranged in at least one annulus row, each said annulus row having a same first number of cells, the first number defining a first cell density, and an aortic section adjacent the distal end, the aortic section having cells arranged in at least one aortic row, each said aortic row having a same second number of cells, the second number defining a second cell density, the first cell density being greater, less or equal to the second cell density.

In some embodiments, a prosthetic heart valve for replacing a native valve includes a collapsible and expandable stent extending between a proximal end and a distal end, the stent including an annulus section adjacent the proximal end, the annulus section having cells arranged in at least one annulus row, each said annulus row having a same first number of cells, the first number defining a first cell density, and an aortic section adjacent the distal end, the aortic section having cells arranged in at least one aortic row, each said aortic row having a same second number of cells, the second number defining a second cell density, the first cell density and the second cell density being different, and a valve assembly disposed within the stent.

In some examples, the first cell density is greater than the second cell density; and/or the first cell density is equal to twelve cells per row; and/or the second cell density is equal to nine cells per row; and/or the cells in each said annulus row are smaller than the cells in each said aortic row; and/or a transition section is disposed between the annulus section and the aortic section, the transition section having cells arranged in at least one transition row, the number of cells per transition row defining a third cell density that is different from the first cell density and the second cell density; and/or the transition section includes multiple rows of cells; and/or the stent further includes a plurality of commissure features and the transition section includes a plurality of cells of a first size and a plurality of asymmetric cells of a second size larger than the first size, each directly adjoining one of the commissure features; and/or each of the commissure features is flanked by an asymmetric cell of the second size on either side of the commissure feature; and/or selected ones of the struts defining cells of the transition section have a thickness that is less than a thickness of the struts in the annulus section; and/or the selected ones of the struts are disposed in a V-shaped pattern.

In some embodiments, a collapsible and expandable stent for a prosthetic heart valve, the stent having a proximal end and a distal end includes an annulus section adjacent the proximal end, and the annulus section having cells arranged in at least one annulus row, each said annulus row having a same first number of cells, the first number defining a first cell density, and an aortic section adjacent the distal end, the aortic section having cells arranged in at least one aortic row, each said aortic row having a same second number of cells, the second number defining a second cell density, the first cell density and the second cell density being different.

In some examples, the first cell density is greater than the second cell density; and/or the first cell density is equal to twelve cells per row; and/or the second cell density is equal to nine cells per row; and/or the cells in each said annulus row are smaller than the cells in each said aortic row; and/or a transition section is disposed between the annulus section and the aortic section, the transition section having cells arranged in at least one transition row, the number of cells per transition row defining a third cell density that is different from the first cell density and the second cell density; and/or the transition section includes multiple rows of cells; and/or the stent further includes a plurality of commissure features and the transition section includes a plurality of cells of a first size and a plurality of asymmetric cells of a second size larger than the first size, each of the asymmetric cells of the second size directly adjoining one of the commissure features; and/or each of the commissure features is flanked by an asymmetric cell of the second size on either side of the commissure feature.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve for replacing a native valve, comprising:

a collapsible and expandable stent extending between a proximal end and a distal end, the stent including an annulus section adjacent the proximal end, the annulus section having cells arranged in at least one annulus row, each said annulus row having a same first number of cells, the first number defining a first cell density of twelve cells per row, and an aortic section adjacent the distal end, the aortic section having cells arranged in at least one aortic row, each said aortic row having a same second number of cells, the second number defining a second cell density of nine cells per row; and a valve assembly disposed within the stent, wherein each cell in the at least one aortic row is directly coupled to a circumferentially adjacent cell in the at least one aortic row.

2. The prosthetic heart valve of claim 1, wherein the cells in each said annulus row are smaller than the cells in each said aortic row.

3. The prosthetic heart valve of claim 1, further comprising a transition section disposed between the annulus section and the aortic section, the transition section having cells arranged in at least one transition row, the number of cells per transition row defining a third cell density that is different from the first cell density and the second cell density.

4. The prosthetic heart valve of claim 3, wherein the transition section includes multiple rows of cells.

5. The prosthetic heart valve of claim 4, wherein the stent further includes a plurality of commissure features and the transition section includes a plurality of cells of a first size and a plurality of asymmetric cells of a second size larger than the first size, each directly adjoining one of the commissure features.

6. The prosthetic heart valve of claim 5, wherein each of the commissure features is flanked by an asymmetric cell of the second size on either side of the commissure feature.

7. The prosthetic heart valve of claim 3, wherein selected ones of the struts defining cells of the transition section have a thickness that is less than a thickness of the struts in the annulus section.

8. The prosthetic heart valve of claim 7, wherein the selected ones of the struts are disposed in a V-shaped pattern.

9. A collapsible and expandable stent for a prosthetic heart valve, the stent having a proximal end and a distal end, and the stent comprising:

an annulus section adjacent the proximal end, the annulus section having cells arranged in at least one annulus row, each said annulus row having a same first number of cells, the first number defining a first cell density;

an aortic section adjacent the distal end, the aortic section having cells arranged in at least one aortic row, each said aortic row having a same second number of cells, the second number defining a second cell density, the first cell density and the second cell density being different; and a transition section disposed between the annulus section and the aortic section, the transition section having cells arranged in at least one transition row, the number of cells per transition row defining a third cell density that is different from the first cell density and the second cell density, wherein each cell in the at least one aortic row is directly coupled to a circumferentially adjacent cell in the at least one aortic row, wherein the first cell density is greater than the second cell density.

10. The stent of claim 9, wherein the first cell density is equal to twelve cells per row.

11. The stent of claim 9, wherein the second cell density is equal to nine cells per row.

12. The stent of claim 9, wherein the cells in each said annulus row are smaller than the cells in each said aortic row.

13. The stent of claim 9, wherein the transition section includes multiple rows of cells.

14. The stent of claim 9, wherein the stent further includes a plurality of commissure features and the transition section includes a plurality of cells of a first size and a plurality of asymmetric cells of a second size larger than the first size, each of the asymmetric cells of the second size directly adjoining one of the commissure sure features.

15. The stent of claim 14, wherein each of the commissure features is flanked by an asymmetric cell of the second size on either side of the commissure sure feature.

* * * * *